US008460200B2

(12) United States Patent
Harrold

(10) Patent No.: US 8,460,200 B2
(45) Date of Patent: Jun. 11, 2013

(54) PHYSIOLOGIC PARAMETER MONITORING APPARATUS

(75) Inventor: Lewis Norman Harrold, Georgetown, MA (US)

(73) Assignee: Analogic Corporation, Peabody, MA (US)

( * ) Notice: Subject to any disclaimer, the term of this patent is extended or adjusted under 35 U.S.C. 154(b) by 719 days.

(21) Appl. No.: 12/560,701

(22) Filed: Sep. 16, 2009

(65) Prior Publication Data

US 2011/0066040 A1   Mar. 17, 2011

(51) Int. Cl.
  *A61B 5/02* (2006.01)
  *A61B 5/053* (2006.01)

(52) U.S. Cl.
  USPC ............................ 600/506; 600/484; 600/504

(58) Field of Classification Search
  USPC .................. 600/481, 484, 504, 506
  See application file for complete search history.

(56) References Cited

U.S. PATENT DOCUMENTS

| | | | |
|---|---|---|---|
| 6,561,986 B2 * | 5/2003 | Baura et al. | 600/526 |
| 7,149,576 B1 * | 12/2006 | Baura et al. | 607/6 |
| 7,422,562 B2 * | 9/2008 | Hatib et al. | 600/485 |
| 2002/0138014 A1 * | 9/2002 | Baura et al. | 600/526 |
| 2003/0120164 A1 * | 6/2003 | Nielsen et al. | 600/513 |
| 2004/0030261 A1 * | 2/2004 | Rantala | 600/561 |
| 2005/0177062 A1 * | 8/2005 | Skrabal et al. | 600/547 |
| 2005/0187481 A1 * | 8/2005 | Hatib et al. | 600/485 |
| 2007/0293770 A1 * | 12/2007 | Bour et al. | 600/481 |
| 2009/0099424 A1 * | 4/2009 | O'Brien et al. | 600/301 |
| 2009/0292217 A1 * | 11/2009 | Bartnik et al. | 600/523 |
| 2010/0249559 A1 * | 9/2010 | Lovejoy | 600/364 |

OTHER PUBLICATIONS

"Assessment of stroke volume variation for prediction of fluid responsiveness using the modified FloTrac™ and PiCCOplus™ system." Hofer et al. Crit Care. 2008;12(3):R82. Epub Jun. 20, 2008.*
"Validation of the thoracic impedance derived respiratory signal using multilevel analysis." Houtveen et al. International Journal of Psychophysiology 59 (2006) 97-106.*
"An Impedance Cardiography System: A New Design." Wang et al. Annals of Biomedical Engineering, vol. 17, pp. 535-556, 1989.*
"Heart Rate Variability." European Heart Journal (1996) 17, 354-381.*
"Normalization." Jan. 23, 2009. http://web.archive.org/web/20090123205018/http://en.wikipedia.org/wiki/Normalization_(statistics).*
Keren et al. "Evaluation of a noninvasive continuous cardiac output monitoring system based on thoracic bioreactance." Am J Physiol Heart Circ Physiol 293:H583-H589, 2007. First published Mar. 23, 2007.*
De Backer et al. "Influence of Respiratory Rate on Stroke Volume Variation in Mechanically Ventilated Patients." Anesthesiology, V 110, No. 5, May 2009. 1092-7.*

(Continued)

*Primary Examiner* — Navin Natnithithadha
*Assistant Examiner* — Meredith Weare
(74) *Attorney, Agent, or Firm* — Driggs, Hogg, Daugherty & Del Zoppo, Co., LPA

(57) ABSTRACT

A physiologic parameter monitor includes a parameter value determiner that determines a parameter value indicative of a response of a human or animal subject to fluid intake during fluid therapy. The parameter value determiner determines the parameter value based on a signal indicative of a non-invasively obtained state of the subject. The physiologic parameter monitor also includes a display that displays the parameter value in a human readable format.

14 Claims, 4 Drawing Sheets

OTHER PUBLICATIONS

Bendjelid et al. "The respiratory change in preejection period: a new method to predict fluid responsiveness." J Appl Physiol 96:337-342, 2004.*

McGee, William T. "A Simple Physiologic Algorithm for Managing Hemodynamics Using Stroke Volume and Stroke Volume Variation: Physiologic Optimization Program." J Intensive Care Med OnlineFirst, published on Sep. 6, 2009, 9 pages.*

Michard et al., Predicting fluid responsiveness in ICU patients: a critical analysis of the evidence, Chest, Jun. 2002, cover page, pp. 2000-2008, current information page, downloaded from www.chestjournal.org.

Kramer et al., Pulse Pressure Variation Predicts Fluid Responsiveness Following Coronary Artery Bypass Surgery, Chest, Nov. 2004, cover page, pp. 1563-1568, current information page, downloaded from www.chestjournal.org.

Luecke et al., Clinical review: Positive end-expiratory pressure and cardiac output, Critical Care, Dec. 2005, pp. 607-621, vol. 9, No. 6.

Solus-Biguenet et al., Non-invasive prediction of fluid responsiveness during major hepatic surgery, British Journal of Anaesthesia, Sep. 16, 2006, pp. 808-816, vol. 97, No. 6.

Vallet et al., How to Titrate Vasopressors Against Fluid Loading in Septic Shock, Advances in Sepsis, 2008, 6 sheets, vol. 6, No. 2.

Michard, et al., Pulse pressure variation:beyond the fluid management of patients with shock, Critical Care, May 17, 2007, 3 sheets, vol. 11, No. 3, http://ccforum.com/content/11/3/131.

Auler, et al., Online Monitoring of Pulse Pressure Variation to Guide Fluid Therapy After Cardiac Surgery, International Anesthesia Research Society, Apr. 2008, pp. 1201-1206, vol. 106, No. 4.

* cited by examiner

PHYSIOLOGIC PARAMETER MONITORING APPARATUS

TECHNICAL FIELD

The following generally relates to a physiologic parameter monitoring apparatus and is described with particular application to a physiologic parameter monitoring apparatus that determines a physiologic parameter value indicative of a response of a subject to fluid therapy based on a non-invasively obtained physiologic signal such as an impedance cardiographic (ICG) output signal. The physiologic parameter monitoring apparatus may also determine on or more other parameter values.

BACKGROUND

With some physiological states, such as septic shock or post-coronary artery bypass surgery recovery, fluid therapy can be used to improve or preserve cardiac performance, and even mitigate imminent death. Where fluid therapy is utilized, the clinician can manage patient fluid intake based on physiological parameters such as arterial pressure pulse variation (PPV) and stroke volume variation (SVV). These parameters have allowed the clinician to anticipate the response of the patient to the fluid therapy.

Traditionally, both PPV and SVV have been calculated from invasively obtained measurements of stroke volume (SV), blood pressure (BP), and/or respiration. For example, PPV has been calculated based on the difference between measured pulse pressure maximum (PPmax) and measured pulse pressure minimum (PPmin) over the respiratory cycle, where pulse pressure has been manually determined for example, based on the difference between invasively measured systolic and diastolic pressures from heart beat to heart beat. SVV has been calculated based on systolic pressure variation (SPV), which has been calculated based on the difference between an invasively measured systolic blood pressure maximum (SBPmax) and an invasively measured systolic blood pressure minimum (SBPmin), over the respiratory cycle.

Unfortunately, as noted above, both the SV and BP values used to calculate PPV and SVV have been measured invasively. In addition, fluctuations in SV, for example, due to an irregular sinus rhythm or otherwise, may introduce error into the calculations. Furthermore, the respiration data taken during PPV and SVV has been measured under controlled mechanical ventilation, or breathing controlled via a ventilator, and spontaneous breathing may also introduce error into the PPV and SVV results. Furthermore, those calculations have been performed manually by a human (hand calculated), and are not easily plotted, averaged, or trended. Moreover, the hand-calculated results are not real-time values calculated with real-time measurements. As a result, the calculated results may not represent the current state of the subject.

SUMMARY

Aspects of the application address the above matters, and others.

In one aspect, a physiologic parameter monitor includes a parameter value determiner that determines a parameter value indicative of a response of a human or animal subject to fluid intake during fluid therapy. The parameter value determiner determines the parameter value based on a signal indicative of a non-invasively obtained physiologic state of the subject. The physiologic parameter monitor also includes a display that displays the parameter value in a human readable format.

In another aspect, a method includes determining, via a processor, a parameter value indicative of a response of a human or animal subject to fluid intake during fluid therapy based on a non-invasively measured physiologic signal and displaying, via a display, the parameter value in a human readable format.

In another aspect, a computer readable storage medium containing instructions which, when executed by a computer, cause the computer to perform the acts of: determining, based on an ICG signal, a parameter value indicative of a response of a human or animal subject to fluid intake during fluid therapy and displaying the parameter value in a human readable format.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
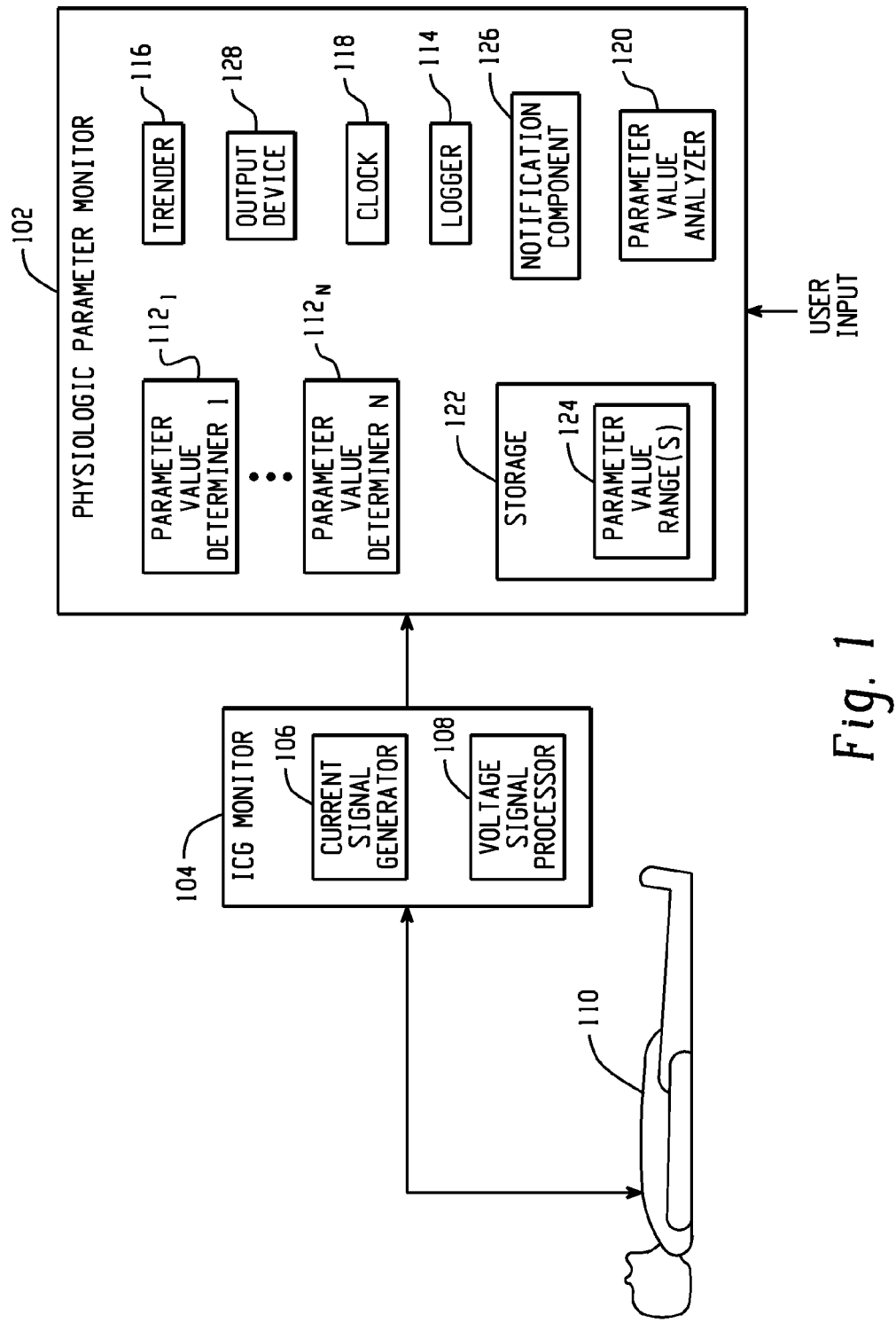
FIG. 1 illustrates an example physiologic monitoring apparatus.

FIG. 1 illustrates a physiologic parameter monitor 102 in connection with an impedance cardiography (ICG) monitor 104.

The ICG monitor 104 includes a current generator 106 and a voltage signal processor 108. The current generator 106 generates a predetermined ICG electrical current signal, which is injected into or applied to a subject 110 via a set of electrodes removeably affixed to the subject. A second set of electrodes removeably affixed to the subject senses a voltage induced by the injected electrical current signal. The voltage signal processor 108 determines an impedance value based on the injected current signal and the sensed voltage signal. The impedance value is indicative of an impedance of the blood flowing from the heart during the heart cycle (a thoracic electric bio-impedance).

The ICG monitor 104 may be a dedicated monitor (as shown) or part of an apparatus that includes both ICG and ECG monitoring, utilizing a common or shared electrode. An example of such a monitor is described in connection with patent application Ser. No. 12/489,156, filed Jun. 22, 2009, and entitled "ICG/ECG monitoring apparatus."

The physiologic parameter monitor 102 includes N parameter value determiners $112_1, 112_2, \ldots, 112_N$, where N is an integer. The N parameter value determiners $112_1, 112_2, \ldots, 112_N$ are collectively referred to herein as parameter value determiners 112. The illustrated parameter value determiner 112 is configured to determine physiologic parameter values in substantially real-time, for example, as the electrical current is injected and the corresponding voltage is sensed. Additionally or alternatively, the parameters can be determined at a time subsequent to their acquisition.

As described in greater detail below, in one instance a parameter value determiner 112 determines at least one parameter value indicative of physiologic information that can be used to facilitate managing fluid and/or drug administration such as a response of a human or animal subject to fluid intake during fluid therapy. In one instance, the at least one parameter value is determined based on the output signal of the ICG monitor 104, which may include one or more of the impedance signal, the injected current signal, and/or the sensed voltage signal. This may allow for determining one or more real-time parameter values for managing fluid management based on non-invasive measurement—the ICG measurement. This may also allow for determining the one or more parameter values without mechanical assistance (e.g., a ventilator).

An event logger 114 allows a user of the monitor 102 to log, at least, an event of interest to the user. The illustrated logger 114 is invoked to log an event based on user input (e.g., push of a button or a key, voice command, etc.). The user input may also include information to log along with the event. The logger 114 may log events in storage such as memory internal to or external from the monitor 102, and the log is accessible for viewing by authorized personnel such as a clinician.

A trender 116 generates time-based trends. The trender 116 can generate a real-time trend in which the trend is generated with data as the data is acquired. The trender 116 can also be used to subsequently process stored data. In the illustrated embodiment, the trender 116 generates trends at least based on the injected current, the sensed voltage, the impedance, information generated therewith, and/or other information, and an output of a clock, such as an internal clock 118 or an external clock. The trender 116 may also trend logged events and/or other information.

A parameter value analyzer 120 analyzes parameter values determined by the parameter value determiner 112. In one instance, the parameter value analyzer 120 compares a determined parameter value with a corresponding predetermined parameter value range. In this instance, the parameter analyzer 120 generates data indicative of whether the parameter satisfies (or is within) the parameter value range.

In the illustrated embodiment, a storage component 122 such as memory stores one or more parameter value ranges 124 for one or more of the parameter value determiners 112, including the above-noted predetermined parameter value range.

A notification component 126 generates notification information (e.g., a message, a warning, an alert, etc.) in response to the data (generated by the parameter value analyzer 120) indicating that the parameter value does not satisfy (or is outside of) the parameter value range. The information may include a visual and/or audible message.

An output device 128 such as a display or other human readable medium presents one or more of the determined parameters, the injected current, the sensed voltage, the impedance, a trend (e.g., via a plot, graph or the like), a logged event, the notification information, and/or other information. The output device 128 may also a printer, a speaker, and/or other output device.

It is to be appreciated that the components 112, 114, 116, 120, and/or 126 can be implemented in hardware and/or software. For example, the components 112, 114, 116, 120, and/or 126 can be or include or be implemented by one or more processors that execute computer executable instructions, corresponding to there respective functions, stored in memory internal to and/or external from the monitor 102.

FIGS. 3, 4, 5, 6, and 7 illustrate example parameter determiners 112, which are discussed in connection with FIG. 2, which depicts an example ICG waveform 200 in relation to an example ECG waveform 214 for a single heartbeat.

Figure 2:
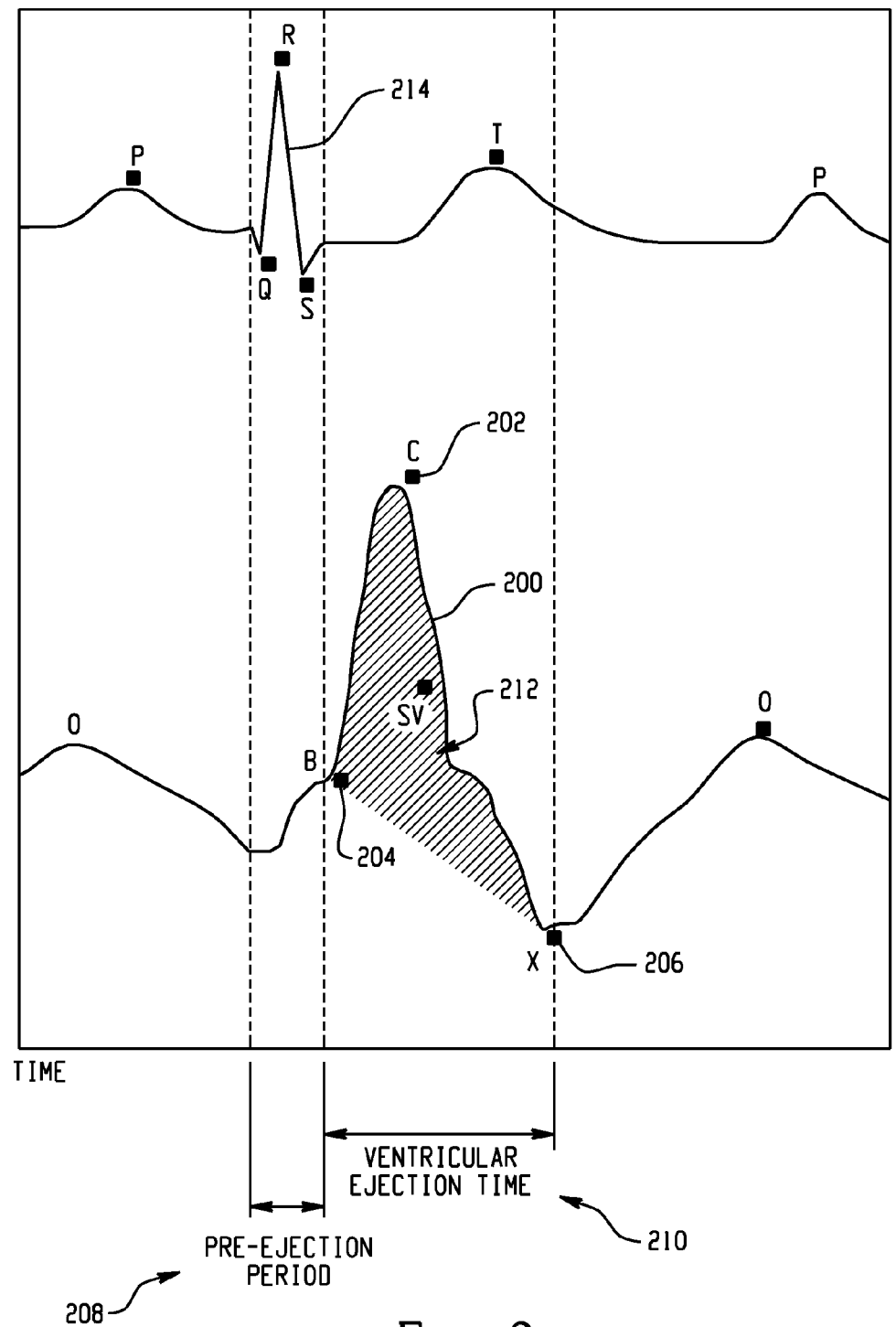
FIG. 2 illustrates an example plot of an ICG signal in relation to an ECG signal as a function of time.

Initially referring to FIG. 2, the ICG waveform 200 indicates peak systolic flow 202, an instance when the aortic valve opens 204, an instance when the aortic valve closes 206, a pre-ejection period (PEP) 208, and a left ventricular ejection period (LVET) 210. The PEP 208 approximately corresponds to the time to fill the left ventricle, and the LVET 210 approximately corresponds to ventricle evacuation time, or the time that blood is ejected from the left ventricle during contraction of the heart.

Figure 3:
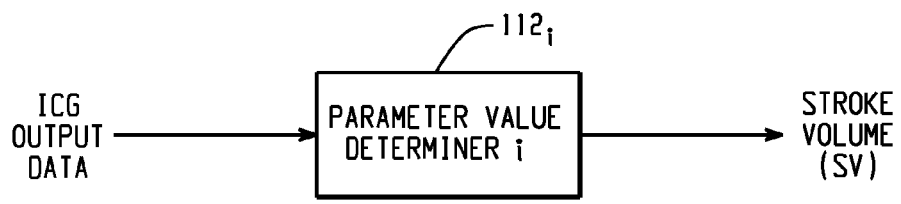
FIG. 3 illustrates an example parameter value determiner for determining a stroke volume value based on ICG measurements.

Referring next to FIGS. 2 and 3, a parameter value determiner $112_i$ determines a stroke volume (SV) value for a plurality of heartbeats based on the ICG output signal. In the illustrated embodiment, the parameter value determiner $112_i$ determines the SV parameter value based on a region 212 the waveform 200 of FIG. 2, which approximately corresponds to the ventricular ejection period 210.

Figure 4:
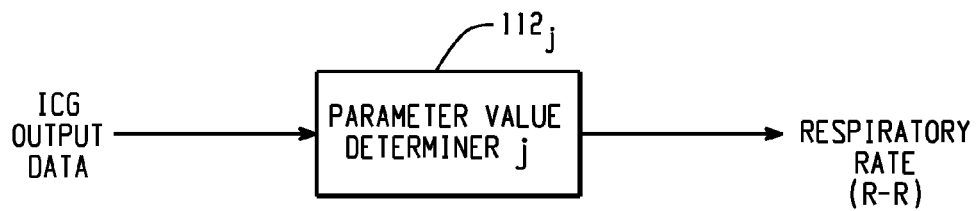
FIG. 4 illustrates an example parameter value determiner for determining a respiratory rate value based on ICG measurements.

Referring to FIGS. 2 and 4, a parameter value determiner $112_j$ determines a respiratory rate (R-R) value based on the ICG output signal. In the illustrated embodiment, the parameter value determiner $112_j$ determines the R-R parameter value based on the peaks 202 for a plurality of heartbeats over a predetermined time period. Additionally or alternatively, the value of the parameter R-R can be determined via a respiratory monitor or other monitor sensing information that can be used to determine the respiratory rate.

Figure 5:
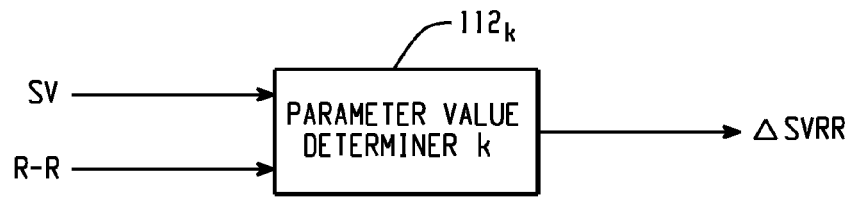
FIG. 5 illustrates an example parameter value determiner for determining a change in stroke volume as a function of respiratory rate based on ICG measurements.

With respect to FIGS. 2 and 5, a parameter value determiner $112_k$ determines a value for physiologic parameter $\Delta$SVRR, which indicates a change in stroke volume (SV) as a function of the respiratory rate (R-R). In one instance, $\Delta$SVRR is calculated based on EQUATION 1:

$$\Delta SV/R\text{-}R. \qquad \text{EQUATION 1}$$

The $\Delta$SVRR parameter value provides information comparable to the information provided by the pressure pulse variation (PPV) and stroke volume variation (SVV) parameters determined via invasively measured physiologic states, for example, for, at least, patient fluid management applications. The SV and/or R-R values determined by the parameter value determiners $112_i$ and $112_j$ can be used by the parameter value determiner $112_k$. Alternatively, the parameter value determiner $112_k$ can determine SV and/or R-R values.

Figure 6:
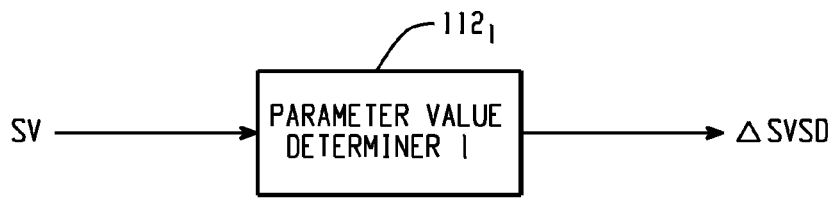
FIG. 6 illustrates an example parameter value determiner for determining a change in stroke volume as a function of the standard deviation of the changes over a time period based on ICG measurements.

With respect to FIGS. 2 and 6, a parameter value determiner $112_l$ determines a value for a physiologic parameter $\Delta$SVSD, which indicates a variability of changes in the stroke volume ($\Delta$SV), as a function of the standard deviation (SD) of the changes over a predetermined time period. The time interval may be based on the respiration rate (R-R) determined over a predetermined number of breaths (e.g., three, ten, twenty five, etc.) or a predetermined amount of time (e.g., 10 seconds, 30 seconds, 5 minutes, etc.). In one instance, $\Delta$SVSD is calculated based on EQUATION 2:

$$\Delta SV*SD \qquad \text{EQUATION 2}$$

The ΔSVSD parameter value provides information comparable to hand-computed variations in peak SV, such as, but not limited to, those used to assess the patient's clinical condition.

Figure 7:
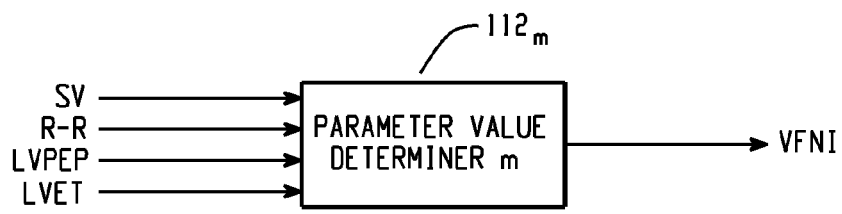
FIG. 7 illustrates an example parameter value determiner for determining a ventricular filling value based on ICG measurements.

With respect to FIGS. 2 and 7, a parameter value determiner $112_m$ determines a value of a physiologic parameter ventricular filling, non-invasive (VFNI), which provides a value representing the ΔSVRR parameter value normalized by a time of filling of the left ventricle. In one instance, the VFNI parameter value is calculated based on EQUATION 3:

$$(\Delta SV/R-R)/(PEP+LVET). \qquad \text{EQUATION 3}$$

It is to be understood that the parameters values discussed in connection with FIGS. 2-7 are examples of parameter values that can be determined by the physiologic parameter monitor 102 and are not limiting; in other embodiments, the physiologic parameter monitor 102 may determined more or less, including the same or different parameter values.

Figure 8:
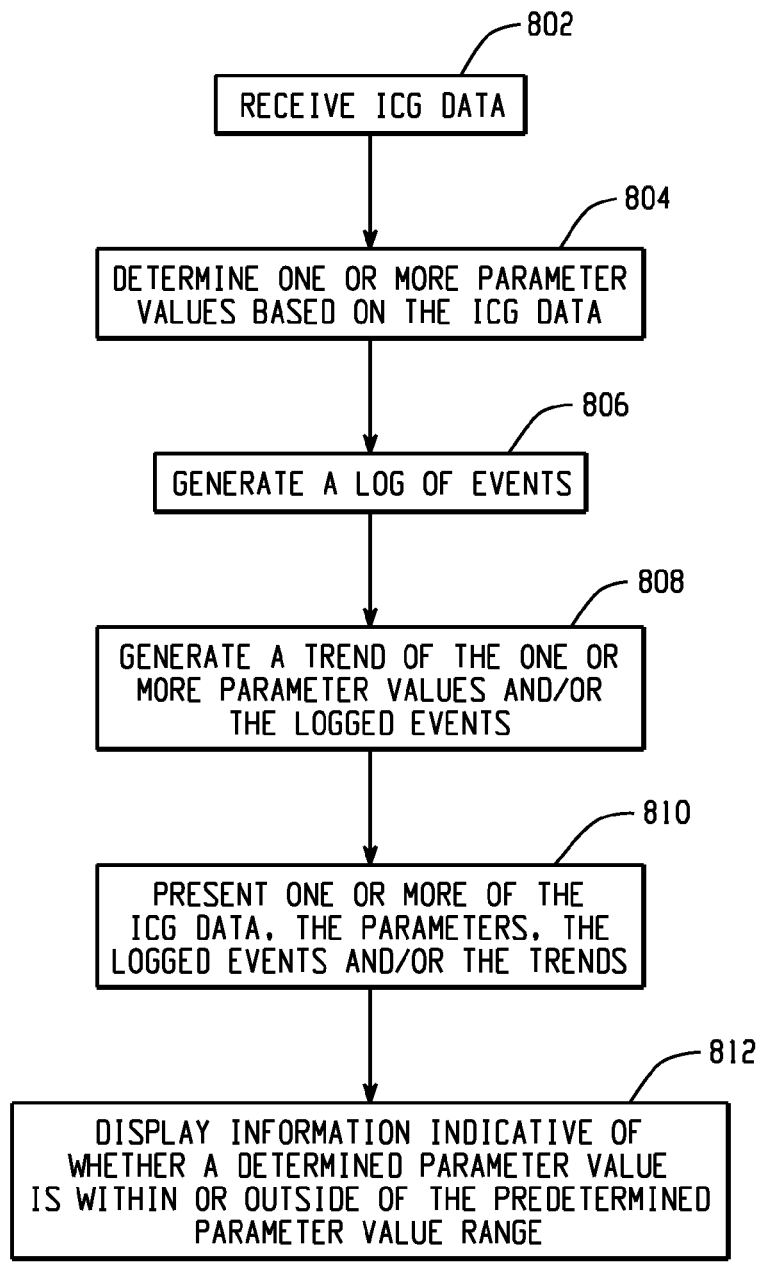
FIG. 8 illustrates a method for determining one or more parameters that facilitate fluid management for a patient.

FIG. 8 illustrates a method for determining parameters that can be used to facilitate fluid management for a patient.

At 802, ICG data is provided to the physiologic parameter value monitor 102. It is to be appreciated that this data can be provided to the monitor 102 in real-time, as it is acquired, and/or otherwise.

At 804, the physiologic parameter value monitor 102 determines one or more parameter values based on the ICG output signal. Examples of such parameter values include, but are not limited to, the parameter values discussed in connection with FIGS. 3-7. The one or more parameter values can be determined in real-time, as the signal is acquired, and/or otherwise.

At 806, the logger 114 generates a log of at least one event. The event may include a present state of the patient, a parameter indicative of the fluid treatment, a parameter indicative of a response to the fluid treatment, information provided by a user, and/or other information. In another embodiment, act 808 is omitted.

At 808, the trender 116 generates a trend of at least one of the parameter values over time. Alternatively or additionally, the trender 116 generates a trend of the logged events. As with the above acts, the trend can be determined in real-time, as the data is available, and/or otherwise. In another embodiment, act 808 is omitted.

At 810, the one or more parameter values are presented via the output device 128. Additionally or alternatively, at least a subportion of the log can be presented. Additionally or alternatively, a trend may be presented. The information presented can be presented in real-time and/or otherwise.

At 812, the one or more parameter values are analyzed to determine whether the parameter values are within or outside of corresponding predetermined parameter value ranges, and the results of the analysis are presented via the output device 128. In another embodiment, act 812 is omitted.

The above may be implemented by way of computer readable instructions, which when executed by a computer processor(s), cause the processor(s) to carry out the acts. The instructions can be stored in a computer readable storage medium associated with or otherwise accessible to the relevant computer.

Suitable application include, but are not limited to, patients in the Emergency Department (ED), for example, during triage, during or after out patient surgery, and/or other application in which it is desirable to monitor and manage fluid intake of a patient.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A physiologic parameter monitor, comprising:
    a processor that determines a parameter value indicative of a response of a human or animal subject to fluid intake during fluid therapy based on an impedance cardiographic (ICG) output signal, wherein the processor is configured to:
        determine a stroke volume value, for a plurality of heartbeats, based on an area under respective ICG output signal waveforms from when the aortic valve opens to when the aortic valve closes;
        determine a respiratory rate value, for the plurality of heartbeats, based on peaks of the respective ICG output signal waveforms over a predetermined time period; and
        determine the parameter value based at least on the determined stroke volume value and the determined respiratory rate value as a change in the determined stroke volume divided by the determined respiratory rate; and
    a display that displays the parameter value in a human readable format.

2. The physiologic parameter monitor of claim 1, wherein the parameter value is normalized by a filling time of the left ventricle of the heart of the subject.

3. The physiologic parameter monitor of claim 1, further comprising a logger that logs an event corresponding to the fluid therapy.

4. The physiologic parameter monitor of claim 1, further comprising a trender that trends the parameter value over time.

5. The physiologic parameter monitor of claim 1, further comprising a parameter analyzer and storage that stores a predetermined desired parameter value range, wherein the parameter analyzer compares the parameter value and the parameter value range and generates data indicative of whether the parameter value is within the parameter value range.

6. The physiologic parameter monitor of claim 5, wherein the display displays the parameter value range concurrently with the parameter value.

7. The physiologic parameter monitor of claim 5, further comprising a notification component that generates a message in response to the parameter value being outside of the parameter value range, and the display displays the message.

8. A method, comprising:
    determining, via a processor, a respiratory rate value based on an impedance cardiographic (ICG) signal non-invasively determined by an ICG monitor monitoring a subject, wherein the respiratory rate value is determined from peaks of the ICG signal corresponding to a plurality of heartbeats over a predetermined time period;
    determining, via the processor, a stroke volume value based on the ICG signal, wherein the stroke volume value is determined for the plurality of heartbeats based on an area under respective ICG output signal waveforms from when the aortic valve opens to when the aortic valve closes;
    determining, via the processor, a parameter value indicative of a response of a human or animal subject to fluid intake during fluid therapy based at least on the respiratory rate value as a ratio of a change in the stroke volume value to the respiratory rate value; and
    displaying, via a display, the parameter value in a human readable format.

9. The method of claim 8, wherein the ratio is normalized by a filling time of the left ventricle of the heart of the subject.

10. The method of claim 8, further comprising:
generating a trend of the parameter value over time; and
displaying the trend.

11. The method of claim 8, further comprising:
logging an event corresponding to the fluid therapy; and
displaying the logged event.

12. The method of claim 8, further comprising:
concurrently displaying a predetermined parameter value range.

13. The method of claim 12, further comprising:
determining whether the parameter value satisfies the parameter value range; and
presenting information indicating that the parameter value does not satisfy the parameter value range in response to the parameter value not satisfying the parameter value range.

14. A non-transitory memory containing instructions which, when executed by a computer, cause the computer to:
determine a stroke volume value, for the plurality of heartbeats, based on an area under respective ICG signal waveforms from when the aortic valve opens to when the aortic valve closes;
determine a respiratory rate value based peaks of the ICG signal corresponding to the plurality of heartbeats over a predetermined time period;
determine a parameter value indicative of a response of a human or animal subject to fluid intake during fluid therapy as a ratio of a change in the stroke volume value to the respiratory rate value based on the determined stroke volume value and the determined respiratory rate value; and
displaying the parameter value in a human readable format.

\* \* \* \* \*